United States Patent [19]
Phan

[11] Patent Number: 5,769,782
[45] Date of Patent: Jun. 23, 1998

[54] MEASURED RETRACTOR

[76] Inventor: Charlie Dung Phan, 17027 E. Cypress St., Covina, Calif. 91722

[21] Appl. No.: 847,945

[22] Filed: Apr. 28, 1997

[51] Int. Cl.⁶ .................................................. A61B 17/02
[52] U.S. Cl. ........................................................ 600/202
[58] Field of Search .................................. 600/201, 202, 600/219, 226

[56]  References Cited

U.S. PATENT DOCUMENTS

| | | |
|---|---|---|
| 1,441,298 | 1/1923 | Pineiro . |
| 4,344,420 | 8/1982 | Forder . |
| 4,934,352 | 6/1990 | Sullivan, Jr. ........................ 600/226 X |
| 4,971,036 | 11/1990 | Collins ..................................... 600/202 |
| 5,035,232 | 7/1991 | Lutze et al. . |
| 5,297,538 | 3/1994 | Daniel . |
| 5,603,689 | 2/1997 | Lucini ..................................... 600/201 |

*Primary Examiner*—Jeffrey A. Smith
*Attorney, Agent, or Firm*—Goldstein & Associates

[57]  ABSTRACT

A retractor comprising a first blade and a second blade, the first blade and second blade having a first blade tip and second blade tip, respectively. The first blade and second blade attach at a pivot point for allowing the first blade tip and second blade tip to move toward and away from each other to create an opening having an opening magnitude. The second blade has a ruler extension having ruler indicia, and the first blade has an arrow end opposite the first blade tip. The arrow end refers to the ruler indicia to indicate the opening magnitude of the retractor. The second blade has a handle track. A handgrip is attached to a bar which is slidably mounted in the handle track. The ruler indicia on the second blade also extends along the handle track.

9 Claims, 3 Drawing Sheets

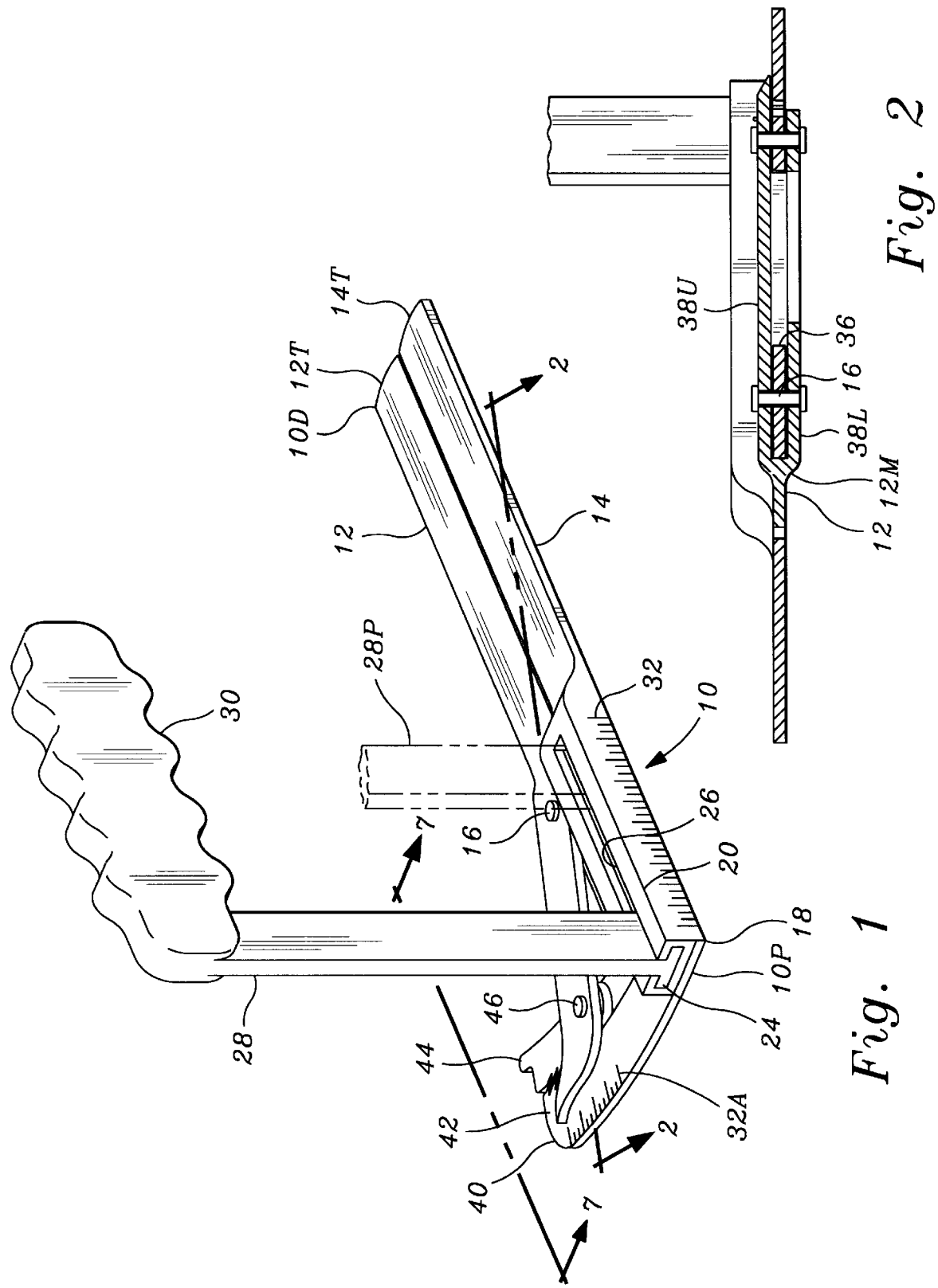

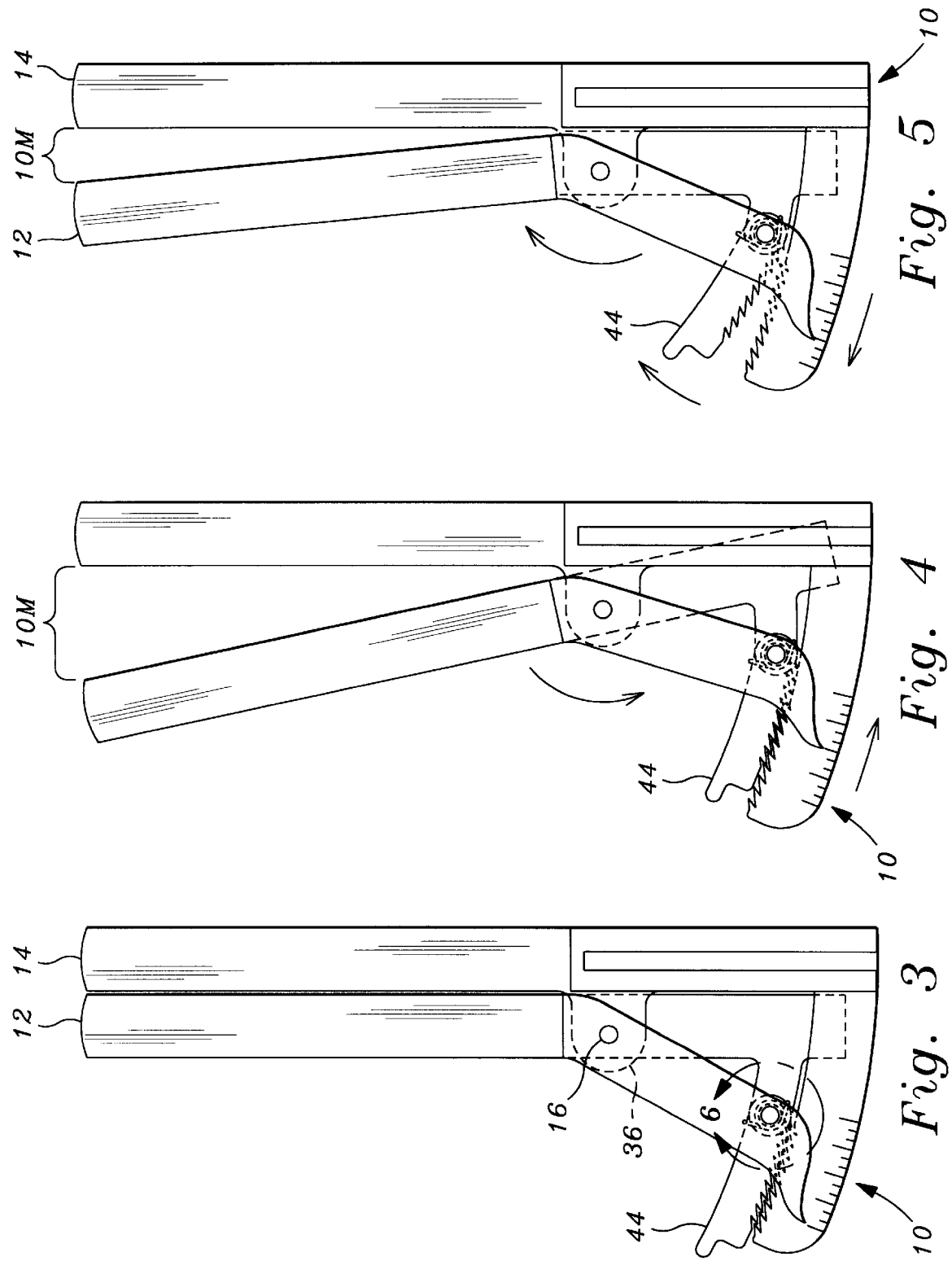

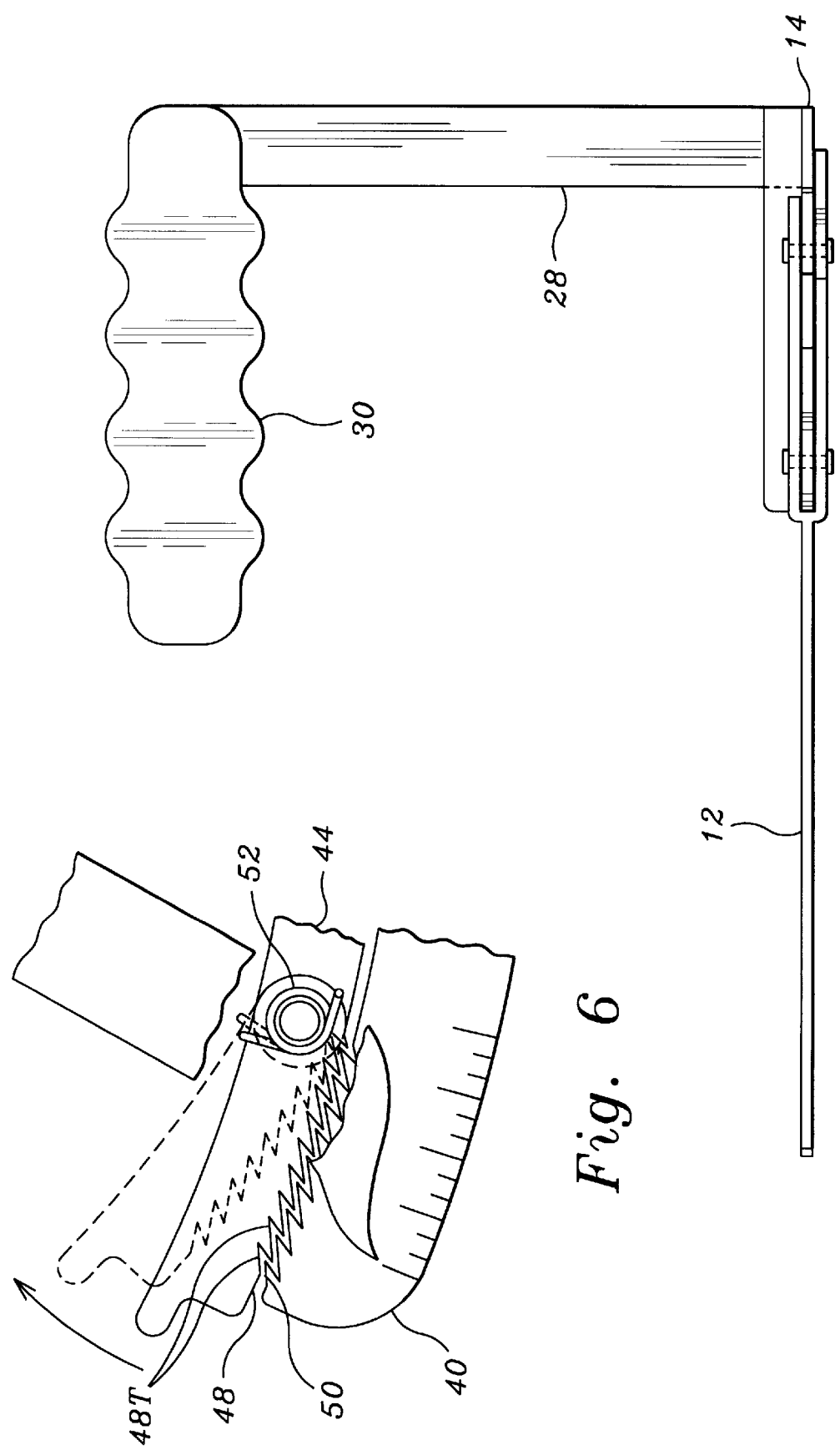

MEASURED RETRACTOR

BACKGROUND OF THE INVENTION

The invention relates to a measured retractor. More particularly, the invention relates to a retractor that is capable of retracting an organ during surgery, in which the amount of retraction may be precisely set beforehand, or measured afterwards.

Retraction is an important part of surgery. In order to effectively work on the target area, the surgeon and his assistants must first move skin, tissue, and other organs out of the way.

In addition, often during surgery it is desirable to make a precise measurement of the width, depth, or height of a cavity. Conventional retracting devices do not have provisions for making such a measurement, nor do they allow the user to precisely measure and control the amount of retraction desired.

While these units may be suitable for the particular purpose employed, or for general use, they would not be as suitable for the purposes of the present invention as disclosed hereafter.

SUMMARY OF THE INVENTION

It is an object of the invention to produce a retractor having retractor prongs capable of being inserted into a surgical cavity, and of retracting skin and other organs a measured amount.

It is another object that the retractor will hold its position at a desired setting. The setting may be changed by lifting a locking lever, adjusting the retractor opening magnitude, and then releasing the locking lever to hold the new setting. The locking lever is spring loaded to always maintain the relative position of the prongs unless the locking lever is being held open by the user.

It is a further object of the invention that the retractor has ruler indicia which allows the user to determine the depth that the retractor has been extended into the surgical cavity.

It is yet a further object of the invention that the prongs may be used as a measuring device by opening the prongs to the width or height of a surgical cavity, and then referring to the ruler indicia to determine the desired measurement from the opening magnitude.

It is a still further object of the invention to reduce intrusion to the body and tissue damage by keeping the pivot point near the entrance to the surgical cavity, and keeping larger components of the retractor outside of the body.

Thus, although a large degree of retraction might be obtained at the desired point of retraction, the size of the retractor near the surgical opening is small.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic perspective view, illustrating the invention.

FIG. 2 is a cross sectional view taken along line 2—2 in FIG. 1.

FIG. 3 is a top plan view, illustrating the retractor in the closed position, wherein the first blade tip and second blade tip are touching.

FIG. 4 is a top plan view, wherein the retractor is being opened.

FIG. 5 is a top plan view, similar to FIG. 4, wherein the retractor is being closed.

FIG. 6 is a top plan view with parts broken away, taken generally in the direction of circle 6 in FIG. 3, showing alternate positions for the control finger.

FIG. 7 is a side elevational view of the retractor, taken in the direction of arrow 7 in FIG. 1.

DETAILED DESCRIPTION OF THE PREFERRED EMBODIMENTS

FIG. 1 illustrates a retractor 10 having a first blade 12 and a second blade 14. The first blade 12 and second blade 14 are pivotally attached at a pivot point 16, allowing pivotal movement between the first blade 12 and second blade 14. The retractor 10 has a distal end 10D and a proximal end 10P. The first blade 12 and second blade 14 have a first blade tip 12T and a second blade tip 14T at the distal end 10D of the retractor 10.

The second blade 14 has a butt 18 having a handle assembly 20. The butt 18 is the proximal end of the second blade 14. The handle assembly 20 includes a handle track 24, the handle track having a slot 26 which extends fully distally along the second blade 14. The handle assembly 20 also has a bar 28 which is slidably mounted inside the handle track 24. The bar 28 extends out the slot 26, and is terminated by a hand grip 30. The bar 28 extends perpendicular to the second blade 14, and the hand grip 30 extends parallel to the second blade 14. The position of the hand grip 30 with respect to the first blade 12 and second blade 14 is alterable by sliding the bar 28 within the handle track 24. This allows the position of the hand grip 30 to be altered while the retractor 10 is being inserted into a body cavity, to provide the user with the maximum leverage at the hand grip 30. FIG. 1 illustrates in phantom an alternate position 28P for the bar 28, which supports the hand grip 30 in an alternate position. Ruler indicia 32 is present along the second blade 14, along the length of the handle track 24. The ruler indicia 32 along the second blade 14 allows the user to determine the depth that the retractor 10 has been inserted into the body cavity.

Referring to FIG. 3, the first blade 12 extends parallel to the second blade 14 when the retractor 10 is in a closed position. The retractor 10 is capable entering an open position, wherein an acute angle is formed between the first blade 12 and second blade 14. Referring momentarily to FIG. 4, the retractor 10 has an opening magnitude 10M, which is defined as the distance between the first blade tip 12T and the second blade tip 14T. The ability for the retractor 10 to exist in either the open position or the closed position derives from the pivot point 16, which attaches the first blade 12 to a pivot extension 36 on the second blade 14. The pivot point 16 is actually a pin, bolt, or the like, that extends through the first blade 12 and pivot extension 36 of the second blade 14.

Referring to FIG. 2, the first blade 12 divides into a first blade upper 38U and a first blade lower 38L at a first blade midpoint 12M. The pivot extension 36 extends perpendicular to the second blade lower, which is then sandwiched between the first blade lower 38L and first blade upper 38U. The pivot point 16 extends through the first blade lower 38L, the pivot extension 36, and then the first blade upper 38U.

Referring back to FIG. 1, a ruler extension 40 extends laterally from the second blade 14 at the proximal end 10P of the retractor 10. The ruler extension 40 extends substantially perpendicular to the second blade 14 but tends to curve radially from the pivot point 16. The first blade 12 has an arrow end 42 at the proximal end 10P of the retractor 10. The arrow end 42 sweeps across the ruler extension 40 as the retractor 10 is varied between the open and closed positions. The position of the arrow end 42 on the ruler extension 40 indicates the opening magnitude, which is zero for the relative position of the first blade 12 and second blade 14 illustrated in FIG. 1. The ruler extension 40 has ruler indicia 32A that is calibrated to correctly indicate the opening magnitude by the position of the arrow end 42.

A control finger 44 is pivotally attached to the first blade 12 near the arrow end 42 with a control finger pin 46. Referring to FIG. 6, the control finger 44 has a toothed edge 48. The ruler extension 40 has a mating teeth edge 50 which matches the toothed edge 48 on the control finger 44 The control finger 44 has a spring 52 which biases the control finger 44 against the ruler extension 40, urging the toothed edge 48 against the mating teeth edge 50, locking the position of the control finger 44, thereby locking the position and magnitude of the retractor opening. FIG. 6 illustrates alternate positions for the control finger 44, whereby the control finger 44 is selectively locked and disengaged.

FIG. 3, FIG. 4, and FIG. 5 illustrate various positions of the retractor 10, wherein the retractor 10 is fully closed in FIG. 3; partially open in FIG. 5; and open halfway in FIG. 4.

In FIG. 3 the control finger 44 is locked against the ruler extension 40, maintaining the retractor in the fully closed position wherein the first blade 12 and second blade 14 extend substantially parallel to each other. In FIG. 5, the control finger 44 is lifted by the operator, freeing the toothed edge 48 from the mating teeth edge 50, allowing the retracting opening magnitude 10M to be adjusted freely. The first blade 12 and second blade 14 form an acute angle. In FIG. 4, the control finger 44 has been released, substantially locking the retractor 10 in the open position, at the opening magnitude selected.

Referring to FIG. 6, it is apparent that the toothed edge 48 and mating teeth edge 50 can be configured to allow the retractor 10 to be opened, or to increase the opening of the retractor 10, even when the control finger 44 is in its locked position. In other words, the toothed edge 48 comprises teeth 48T which are angled to allow motion that tends to increase the opening magnitude, without disengaging the toothed edge 48 from the mated teeth edge 50, but which will prevent the retractor 10 from closing without first freeing the toothed edge 48. Proper angling for achieving this goal involves angling the teeth 48T on both the toothed edge 48 and mating teeth edge 50 toward the pivot point 52 as illustrated in FIG. 3 through FIG. 5.

FIG. 7 is a side view, illustrating the retractor 10. The hand grip 30 is fully proximal. The bar 28 allows the hand grip 30 to extend parallel to the first blade 12 and second blade 14, but allows the same to be supported at a considerable distance, allowing the surgeon to work without interference by the assistant who is holding the retractor 10.

In general, the retractor 10 is operated by opening the retractor 10 either prior to, or after the retractor 10 is inserted into a surgical cavity. The degree in which the retractor 10 is opened may be precisely controlled by observing the ruler indicia 32A on the ruler extension 40, and the position indicated by the arrow end 42. Conversely, the width and height of the surgical cavity may be precisely measured by opening the retractor 10 to said width or height, and then observing the position of the arrow end 42 on the ruler indicia 32A on the ruler extension 40. In addition, the depth of a surgical cavity, or the depth that the retractor 10 is inserted into a surgical cavity may be controlled and/or measured by observing the ruler indicia 32 along the handle track 24 on the second blade 14.

It can be seen that the degree of intrusion and tissue damage is minimal, since the retractor is widest at the first blade tip 12T and second blade tip 14T. Because of the location of the pivot point 16, the retractor would tend to be narrower travelling in the proximal direction, back toward the surgical opening. Thus the retractor 10 can be used to provide a considerably greater amount of retraction than the size of the opening to the surgical cavity.

In conclusion, herein is presented a retractor 10 which provides precise, measured control over the degree of retracting, is non-intursive, and which allows a surgeon and surgical assistants to make precise measurements during a surgical procedure.

What is claimed is:

1. A retractor, having a proximal end and a distal end, comprising:

a first blade having a first blade tip, and an arrow end opposite the first blade tip;

a second blade having a second blade tip, the second blade attached to the first blade at a pivot point for allowing the first blade tip and second blade tip to move toward and away from each other to create an opening having an opening magnitude, the second blade having a ruler extension, the ruler extension having ruler indicia, and said arrow end refers to the ruler indicia on the ruler extension to indicate the magnitude of opening between the first blade tip and second blade tip;

a handle assembly, the handle assembly comprising a hand grip extending parallel to the second blade, and a bar extending between the hand grip and second blade, said bar extending perpendicular to both the hand grip and the second blade.

2. The retractor as recited in claim 1, wherein the second blade further comprises a handle track, the bar capable of sliding proximal and distally in the handle track.

3. The retractor as recited in claim 2, wherein the first blade further comprises a first blade upper and first blade lower, the second blade having a pivot extension, the pivot point is a pin that extends through the first blade upper, through the pivot extension, and then through the first blade lower.

4. The retractor as recited in claim 3, wherein the first blade further comprises a control finger, the control finger selectively engaging the ruler extension for locking the position of the retractor wherein the opening magnitude is fixed.

5. The retractor as recited in claim 4, wherein the control finger has a spring, the spring biasing the control finger against the ruler extension to maintain the control finger in a normally locked position.

6. The retractor as recited in claim 5, wherein the control finger has a toothed edge and the ruler extension has a mating teeth edge, the toothed edge engages the mated teeth edge to lock the control finger.

7. The retractor as recited in claim 6, wherein the toothed edge has teeth, said teeth angled in the direction of the pivot point so that the retractor can be opened without disengaging the toothed edge from the mated teeth edge but the retractor will not close unless the toothed edge is disengaged from the mated teeth edge.

8. The retractor as recited in claim 7 wherein ruler indicia is also present along the second blade, said ruler indicia extending proximal to distally to allow measurement of insertion depth into a body cavity.

9. The retractor as recited in claim 8, wherein the ruler indicia on the second blade extends along the handle track.

* * * * *